(12) United States Patent
Ueda et al.

(10) Patent No.: US 7,198,701 B2
(45) Date of Patent: Apr. 3, 2007

(54) NUCLEIC ACID ANALYZING METHOD

(75) Inventors: Masanori Ueda, Tokushima (JP); Hirohisa Abe, Kyoto (JP); Yoshinobu Baba, Tokushima (JP)

(73) Assignee: Japan Science and Technology Corporation, Kawaguchi-shi (JP)

( * ) Notice: Subject to any disclaimer, the term of this patent is extended or adjusted under 35 U.S.C. 154(b) by 670 days.

(21) Appl. No.: 10/432,960

(22) PCT Filed: Nov. 29, 2000

(86) PCT No.: PCT/JP00/08413

§ 371 (c)(1),
(2), (4) Date: May 29, 2003

(87) PCT Pub. No.: WO02/44708

PCT Pub. Date: Jun. 6, 2002

(65) Prior Publication Data
US 2004/0094419 A1 May 20, 2004

(51) Int. Cl.
G01N 27/447 (2006.01)

(52) U.S. Cl. ..................... 204/451; 204/455

(58) Field of Classification Search ........ 204/601–605, 204/451–455, 577, 643, 608, 609, 457, 458
See application file for complete search history.

(56) References Cited

U.S. PATENT DOCUMENTS

| 4,737,251 A | 4/1988 | Carle et al. ............... 204/458 |
| 5,178,737 A | 1/1993 | Lai ........................... 204/455 |
| 5,599,432 A | 2/1997 | Manz et al. ................ 204/451 |
| 2002/0098504 A1 | 7/2002 | Huang et al. .................. 435/6 |

FOREIGN PATENT DOCUMENTS

| DE | 4314755 A1 | * 11/1994 |
| EP | 457748 A | 11/1991 |
| JP | 07-043344 A | 2/1995 |
| JP | 11-148919 A | 6/1999 |

OTHER PUBLICATIONS

Derwent abstract of DE 4314755 A1.*
Kim et al. ("Pulsed Filed Capillary Electrophoresis of Multikilobase length Nucleic Acids in Dilute Methyl Cellulose Solutions," Anal. Chem. 1994, 66, 3081-3085).*
Simpson, P.C. et al., PNAS, vol. 95, pp. 2256-2261 (1998).
Ueda, M. et al., Chromatography, vol. 21, No. 2, pp. 105-106 (2000).
Ueda, M. et al., Electrophoresis, vol. 22, pp. 217-221 (2001).
Kim, Y. and Morris, M.D., Electrophoresis, vol. 17, p. 152-160 (1996).

(Continued)

Primary Examiner—Alex Noguerola
(74) Attorney, Agent, or Firm—Birch, Stewart, Kolasch & Birch, LLP

(57) ABSTRACT

To provide a method for analyzing a nucleic acid according to high throughput microcapillary electrophoresis during microchip electrophoresis under non-steady electric field, the method being capable of detecting polymorphism of a large number of genes at a high speed. The present invention is useful for the diagnosis and treatment of diseases such as detection of gene diseases and application to Taylor-made therapy.

13 Claims, 12 Drawing Sheets

OTHER PUBLICATIONS

Kim Y. and Morris, M.D., Anal. Chem. vol. 66, p. 3081-3085 (1994).

Bakajin, O. et al., Anal. Chem. vol. 73, p. 6053-6056 (2001).

Huang, L.R. et al., Nat. Biotech., vol. 20, p. 1048-1051 (2002).

* cited by examiner a) DC b) 10 Hz

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: A sequence
      for synthesized oligonucleotide, of which nucleotide sequence is
      a partial portion of exon
      7of p53 tumor suppressive gene.

<400> SEQUENCE: 1
gttggctctg actgtaccac                                                20

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: A sequence
      for synthesized oligonucleotide, of which nucleotide sequence is
      a partial portion of exon
      7of p53 tumor suppressive gene.

<400> SEQUENCE: 2
gttggctctg actgtaccac catccactac aactacatgt                          40

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: A sequence
      for synthesized oligonucleotide, of which nucleotide sequence is
      a partial portion of exon
      7of p53 tumor suppressive gene.

<400> SEQUENCE: 3
gttggctctg actgtaccac catccactac aactacatgt gtaacagttc ctgcatgggc    60
```

NUCLEIC ACID ANALYZING METHOD

This application is the national phase under 35 U.S.C. §371 of PCT International Application No. PCT/JP00/08413 which has an International filing date of Nov. 29, 2000, which designated the United States of America.

TECHNICAL FIELD

The present invention relates to a method for analyzing a nucleic acid. More specifically, the present invention relates to a method for analyzing a single-stranded or double-stranded nucleic acid conformation polymorphism according to high throughput non-steady electric field-type microchip electrophoresis such as electric field inversion, the method being capable of detecting polymorphism of a large number of genes at a high speed.

BACKGROUND ART

Conventionally, as an analytical technique employing electrophoresis, there have been performed analyses based on separation by slab gel using a polyacrylamide gel, agarose gel, or the like as a support for separation. The separation by slab gel has some defects such that its resolution is limited by factors such as temperature changes and pH changes during electrophoresis, and that it is unsuitable for analysis of trace samples and automation of devices.

A method for solving the defects includes capillary electrophoresis, which enables automated measurement of trace samples with suppressing the generation of temperature changes. However, the lower limit for the effective length of the existing capillary electrophoresis device is about 8 cm depending upon the construction of the device, so that there is actually a limitation on miniaturization of the device.

On the other hand, with the recent developments in microfabricated device techniques, various DNA analytical devices, including capillary electrophoresis devices have been miniaturized [Becker, H. et al., *Electrophoresis*, 2000, 21, 12–26; Ueda, M. et al., *Anal. Scie.*, 2000, 16, 657–658; Simpson, P. C. et al., *Proc. Natl. Acad. Sci. U.S.A.*, 1998, 95, 2256–2261; Backhouse, C. et al., *Electrophoresis*, 2000, 21, 150–156; Kopp, M. U. et al., *Science*, 1998, 280, 1046–104; Waters, L. C. et al., *Anal. Chem.*, 1998, 70, 158–162; and Han, J. et al., *Science*, 2000, 288, 1026–1029]. Concretely, there have been provided by miniaturization techniques, for instance, a capillary array electrophoresis device [the above-mentioned Simpson et al., *Proc. Natl. Acad. Sci. U.S.A.*; the above-mentioned Backhouse et al., *Electrophoresis*], a PCR-chamber-integrated electrophoresis device [the above-mentioned Kopp, M. U. et al., *Science*; the above-mentioned Waters, L. C. et al., *Anal. Chem.*], and an entropic trap array (gel-free) electrophoresis device [the above-mentioned Han, J. et al., *Science*].

However, there are some defects in the miniaturization techniques such that, for instance, in order to carry out separation excellently under the steady electric field in the sample-separation process, a longer effective length is necessitated [the above-mentioned Han, J. et al., *Science*].

On the other hand, non-steady electric field methods such as electric field inversion method are means which have been performed in ordinary pulse field electrophoresis using agarose gel, and are in many cases used for separation of long-chain DNA of several dozen kilo-base pairs or more.

However, there are some defects in the above-mentioned non-steady electric field methods such that it is difficult to apply the methods to conventional capillary electrophoresis from the viewpoint that an expensive electric power source would be required for high-speed inversion of high electric field.

DISCLOSURE OF INVENTION

An object of the present invention is to provide a method for analyzing a polymer according to non-steady electric field type microchip electrophoresis, more concretely electric field inversion type microchip electrophoresis, more concretely to a method for analyzing a nucleic acid, still more concretely to an analysis method based on the difference in higher-order structure in a single-stranded nucleic acid conformation polymorphism, the method being capable of shortening an effective length in electrophoresis, thereby making it possible to achieve high integration and miniaturization of microchips for electrophoresis, and being capable of performing high-speed analysis of DNA conformation polymorphism, and capable of analyzing trace samples at high sensitivity.

Concretely, the gist of the present invention relates to:

[1] a method for analyzing a nucleic acid, characterized in that the method comprises carrying out electrophoresis under non-steady electric field during electrophoresis on a microchip in microcapillary electrophoresis;

[2] the method for analyzing a nucleic acid according to the above item [1], wherein the non-steady electric field is electric field inversion;

[3] the method for analyzing a nucleic acid according to the above item [2], wherein the method in a microcapillary electrophoresis comprises the steps of:

(a) carrying out electric field inversion during electrophoresis on a microchip, thereby separating each of the nucleic acids having different physicochemical properties, and (b) detecting the nucleic acid separated by the above step (a);

[4] the method for analyzing a nucleic acid according to the above item [2] or [3], wherein a forward/backward time weight in the electric field inversion is 1/1 to 10/1;

[5] the method for analyzing a nucleic acid according to any one of the above items [2] to [4], wherein the electric field inversion is carried out by applying electric field at a frequency of at least 10 Hz;

[6] the method for analyzing a nucleic acid according to any one of the above items [1] to [5], wherein an effective length in electrophoresis is 0.5 to 70 mm;

[7] the method for analyzing a nucleic acid according to any one of the above items [1] to [6], wherein the electric field has the strength of |10| to |100000| (absolute value) V/cm;

[8] the method for analyzing a nucleic acid according to any one of the above items [1] to [7], wherein the microchip is a microchip comprising a sample-injection member, a channel for sample analysis and a reservoir for an electrode;

[9] the method for analyzing a nucleic acid according to the above item [8], wherein the microchip is a chip comprising an upper plate and a lower plate, wherein:

(A) the lower plate has thereon two orthogonal channels of 1 to 200 μm in width and 0.5 to 50 μm in depth, (B) the upper plate has four reservoirs of 0.5 to 4 mm in both diameter and depth, and (C) any one of the reservoirs as defined in (B) is arranged at a position corresponding to each end of the channels as defined in (A), and wherein the reservoir is a reservoir to which the electric field can be applied;

[10] the method for analyzing a nucleic acid according to the above item [9], wherein the channel holds a separation medium containing at least one member selected from the group consisting of methyl cellulose, hydroxypropyl methyl cellulose (HPMC), hydroxyethyl cellulose (HEC), hydroxypropyl cellulose (HPC), polyethylene glycol (PEG), polyethylene oxide (PEO), polyacrylamide (PAA), polyvinyl pyrrolidone (PVP), dextran and agarose;

[11] the method for analyzing a nucleic acid according to the above item [10], wherein pH of the separation medium is 1 to 12;

[12] the method for analyzing a nucleic acid according to the above item [10] or [11], wherein the separation medium is a buffer containing 1% by weight of methyl cellulose, and wherein the buffer is at least one member selected from the group consisting of Tris-borate buffer, Tris-acetate buffer, TAE (Tris-acetate, EDTA) buffer, TBE (Tris-borate, EDTA) buffer, Tris-hydrochloric acid buffer and phosphate buffer;

[13] the method for analyzing a nucleic acid according to any one of the above items [1] to [12], wherein a physicochemical property is at least one member selected from the group consisting of nucleic acid conformation polymorphism, molecular weight and higher-order structure; and

[14] the method for analyzing a nucleic acid according to any one of the above items [1] to [13], wherein the means of detecting the nucleic acid in the step (b) is at least one member selected from the group consisting of ultraviolet/visible light absorption detection, fluorescence detection, differential refractive index detection, thermo-optical detection, circular dichroism detection, electrochemical detection and electroconductivity detection.

BEST MODE FOR CARRYING OUT THE INVENTION

Figure 1:
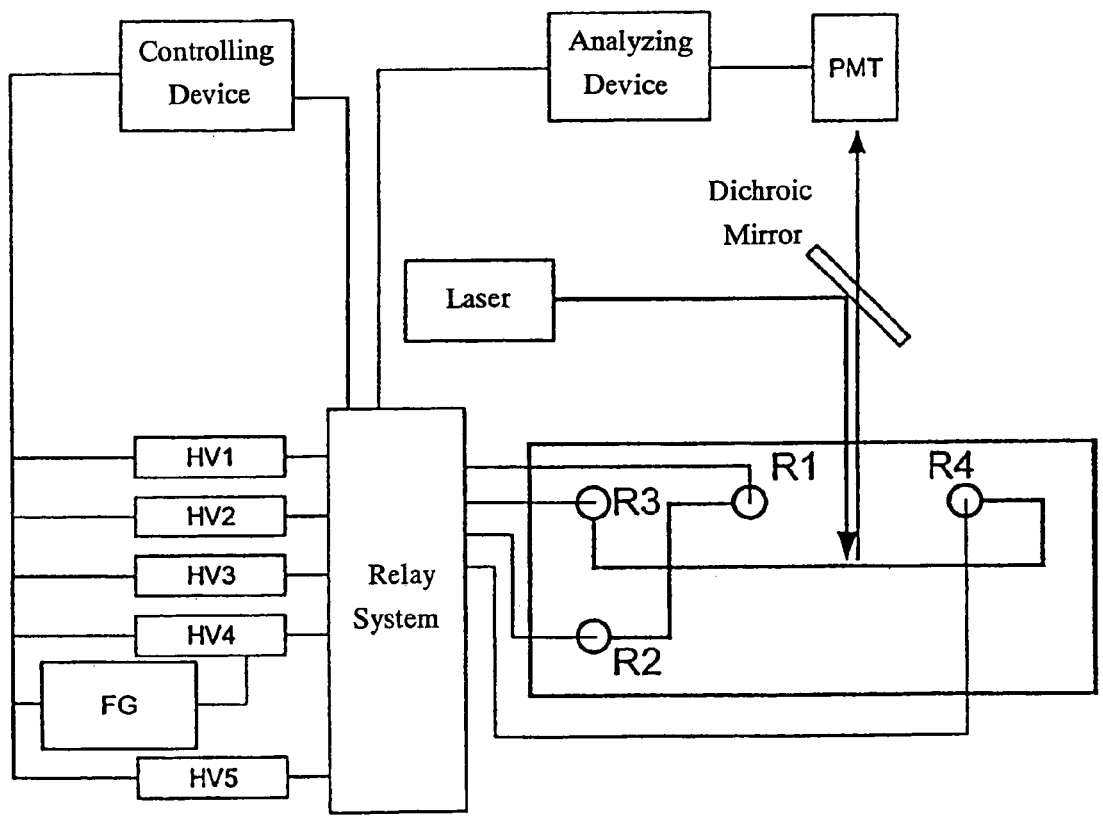
FIG. 1 is a conceptual view of a microcapillary electrophoresis device (hereinafter also referred to as μ-CE) having a laser-excited fluorescence detector. In the figure, FG represents an arbitrary function generator; HV1 to HV5 represent high-voltage power supplies; PMT represents a photomultiplier tube; and R1 to R4 represent reservoirs. The controlling device may be a general-purpose computer in which a device-control software (Labview or the like), or the like is installed. The analyzing device may be a general-purpose computer in which a signal analysis software (CLASS-VP or the like), or the like is installed. The microchip has flow paths for sample loading (R1 and R2) and flow paths for sample analysis (R3 and R4), wherein the potential at each reservoir is controlled by using high-voltage power supplies HV1 to HV5 and a relay system. Since a high-speed switching of electric fields is required in the sample injection, the sample injection is realized by outputting given voltages from the five power supplies in advance, and switching the power supplies by the relay system.

The present invention is based on the surprising findings of the present inventors that DNA separation can be achieved by carrying out electrophoresis under non-steady electric field, especially electric field inversion type (FI) electrophoresis, in a microchip, even at such short effective lengths which had not been able to be separated under ordinary conditions (for instance, steady electric field and the like).

It has already been reported that the electric field inversion method improves the resolution during the electrophoresis of long-chain DNA (50 kbp or more) in gel, or during the capillary electrophoresis of long-chain DNA in a polymer solution ["*THE FRONTIER ELECTROPHORESIS/ THE FRONTIER CHROMATOGRAPHY*," 15, pages 1–9, published on Apr. 2, 1994, by ATTO Corporation, Y. Kim, M. D. Morris, *Electrophoresis* 17, 152–160 (1996)].

However, the findings of the present inventors that high resolution can be exhibited by the electric field inversion method even for DNA as short as about 100 nucleotides, even at a short effective length of 8 cm or less, have been unexpected.

The electric field inversion type electrophoresis method is an electrophoresis method employing electric field inversion to periodically change the direction of the electric field. Concretely, the method is a method in which separation is achieved by setting the period of forward electric field (electric field for transferring the molecule to be analyzed from the starting point of electrophoresis on gel) and backward electric field (electric field for returning the molecule from one point on the gel toward the starting point of electrophoresis), and the duration time of pulse amplitude or strength of applied voltage.

One of the features of the method for analyzing a nucleic acid of the present invention resides in that the method comprises carrying out electrophoresis under non-steady electric field, more concretely electric field inversion, during electrophoresis on a microchip in microcapillary electrophoresis. An embodiment of the method for analyzing a nucleic acid of the present invention includes, for instance, a method for analyzing a nucleic acid comprising the steps of in microcapillary electrophoresis, (a) carrying out electric field inversion during electrophoresis on a microchip, thereby separating each of the nucleic acids depending on physicochemical properties thereof, and
(b) detecting the nucleic acid separated by the above step (a).

According to the method for analyzing a nucleic acid of the present invention, the effective length required for the separation of a nucleic acid, for instance, DNA, can be shortened by a combination of electrophoresis method in microchip with non-steady electric field, concretely with electric field inversion. Therefore, there are exhibited some excellent effects such that further downsizing and higher integration of the microchip can be achieved, that high-speed analysis of conformation polymorphism of DNA [concretely SSCP (single-strand conformation polymorphism)] can be performed, and that trace samples can be analyzed at high sensitivity.

In addition, in the method for analyzing a nucleic acid of the present invention, there are exhibited some excellent effects such that the analysis can be performed at an even shorter capillary length because the microcapillary electrophoresis is applied along with the above-mentioned electric field inversion during the separation of the nucleic acid, and that commercially available electric power supplies that follow electric field inversion at high speeds can be used because the voltage applied to both ends of the microcapillary (used maximally about 10 kV, usually up to about several kV) can be controlled to be low, as compared to existing capillary electrophoresis devices (concretely, maximally about 30 kV).

Figure 10:
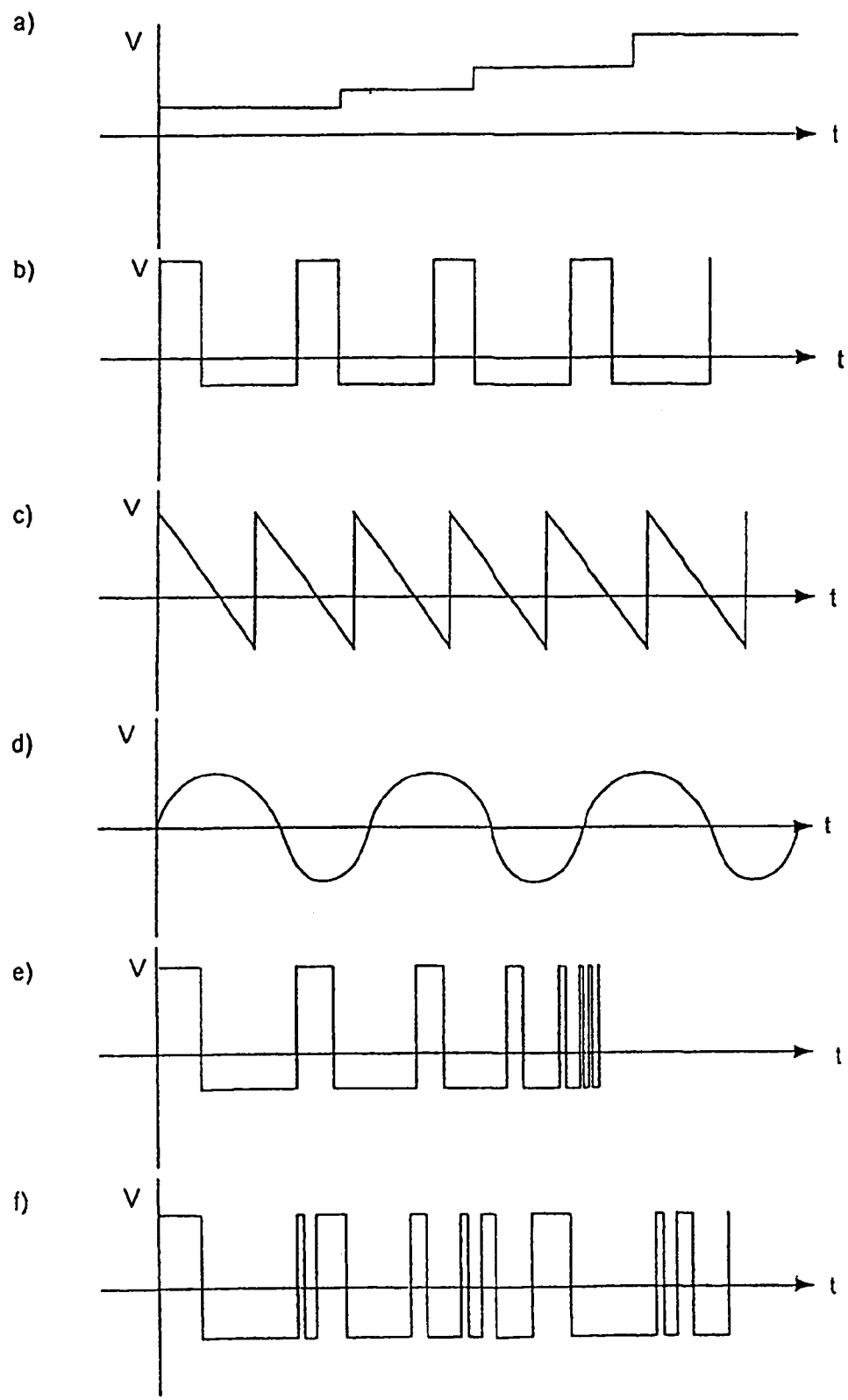
FIG. 10 is a schematic view of non-steady electric field.

The non-steady electric field generically refers to electric field that changes with time. Concretely, as shown in FIG. 10, the non-steady electric field includes electric fields that change periodically in the form of rectangular waves, triangular waves, sine waves and the like, electric fields of which frequency itself is variable, non-periodical electric fields, and the like. All these electric fields can be used for electrophoresis on a microchip in the present invention.

Figure 11:
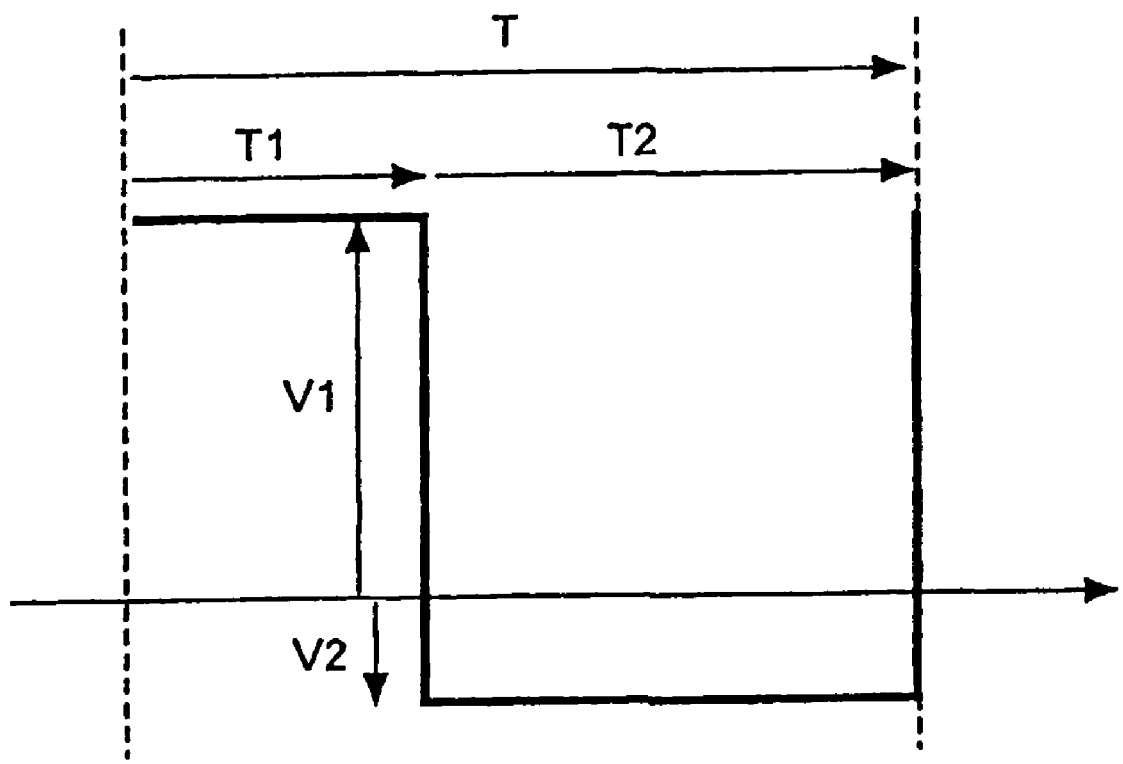
FIG. 11 is a schematic view of parameters of inverted electric field.
Figure 12:
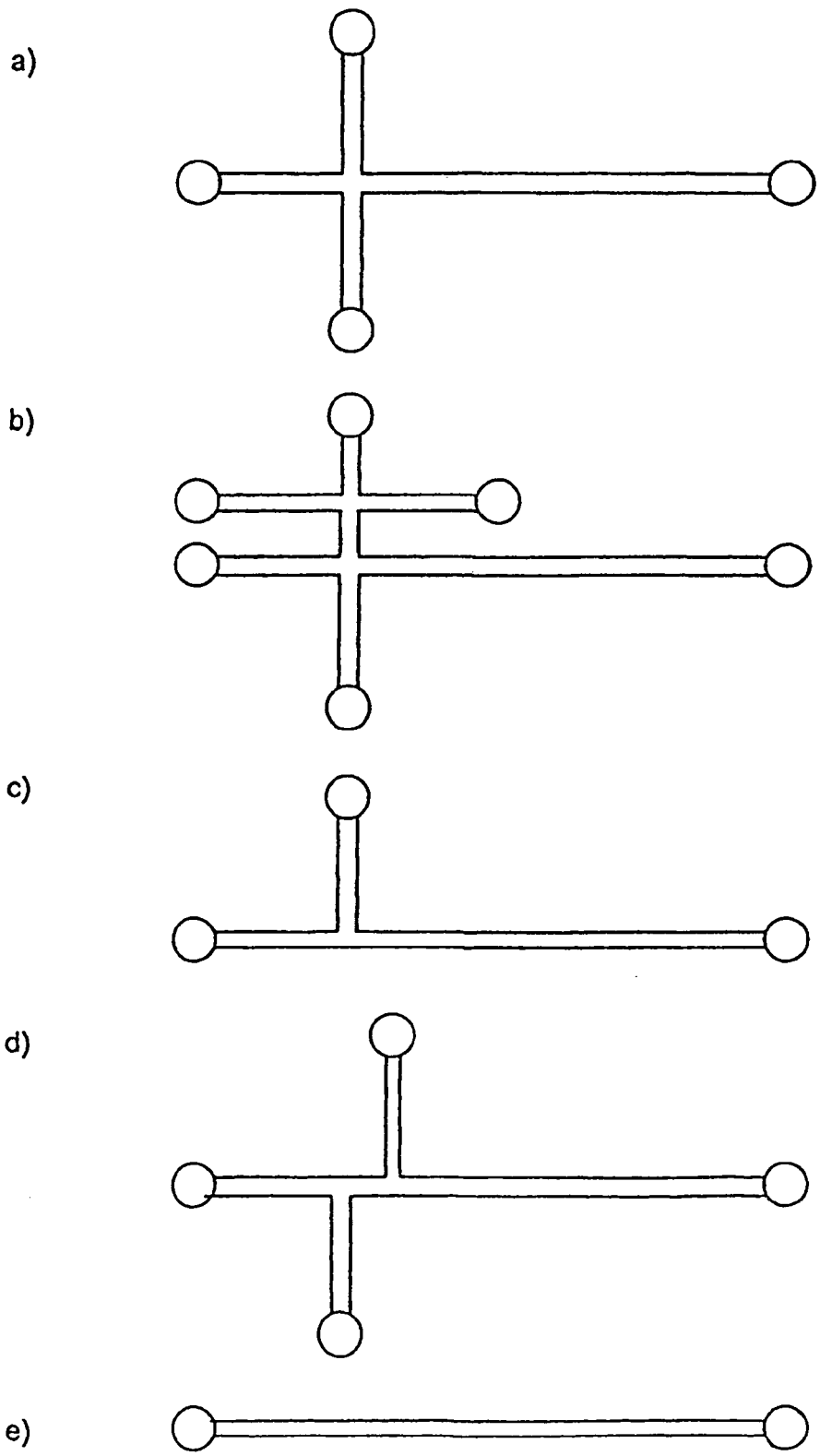
FIG. 12 is a schematic view of the sample-injection member of a microchip electrophoresis device.

In the electric field inversion method, the inverted electric field is generally defined by the parameters shown in FIG. 11, concretely, period T, which is a repeat unit of inversion, time periods T1 and T2 for applying forward and backward electric fields, and forward and backward applied electric fields (voltages) V1 and V2. Although the simplest case of V2 =−V1 will be explained in Examples in the present specification, the above-mentioned parameters can be determined appropriately depending upon the purposes and conditions of the analysis.

The degree of inversion repeat is hereinbelow expressed by frequency, which is a reciprocal of the period, and the degree of inversion is expressed by a pulse coefficient, concretely, forward/backward time weight T1/T2.

Hence, it is preferable that the duration time for pulse amplitude (forward/backward time weight) in electric field inversion is 1/1 to steady electric field, more preferably 1/1 to 10/1, and still more preferably 1/1 to 5/1, from the viewpoints of obtaining an appropriate resolution and allowing the nucleic acid to reach a final migration form. Here, a final migration form of the nucleic acid as used herein means a condition in which the bands of individual nucleic acids are well distinguishable during the separation of the nucleic acids.

In the method for analyzing a nucleic acid of the present invention, the frequency in electric field inversion can be determined by, for instance, electrophoresing a nucleic acid, for instance, a DNA fragment, obtaining a band width Δ and a height h of the relative intensity peak ascribed to the DNA fragment at a migration time t, and finding the frequency at which the value of relative band width Γ=Δ/ht reaches its minimum. Also, in the optimization of frequency for the separation of a nucleic acid, for instance, DNA, the movement of DNA in gel or in a polymer solution responds to the frequency differently depending upon the length thereof, so that the size of the nucleic acid, for instance, DNA, to be analyzed can be one of the important parameters.

Concretely, it is preferable that the frequency is at least 10 Hz from the viewpoint of reduction in dummy peak detection. Concretely, in the case of a short-chain DNA of about 20-mer, it is desired that the frequency is 10 to 30 Hz, preferably 10 to 20 Hz.

The frequency can be generated by, for instance, using a commonly used frequency generator. As a concrete example, in FIG. 1, the frequency can be generated by controlling the potential at the reservoir (R3) relative to R4 (GND) using a frequency generator (FG) and the high-voltage power supply (HV4).

The effective length in electrophoresis can be altered appropriately depending upon the purpose of applications, the above-mentioned frequency, separation medium, pulse coefficient, voltage, and the like. According to the method for analyzing a nucleic acid of the present invention, the effective length can be made shorter, as compared to the effective length of conventional capillary electrophoresis systems (shortest effective length: about 75 mm). Concretely, it is desired that the effective length is 70 mm or less from the viewpoint of miniaturization of the microchip, 35 mm or less from the viewpoint of sufficiently performing high-speed separation, and that the effective length is 0.5 mm or more, from the viewpoint of preventing the sample leakage from the crossing portion of the flow path and the backflow of the injected sample into the crossing portion, more desirably 1 mm or more, from the practical viewpoint.

The electric field to be applied can be set appropriately according to conditions of the nucleic acid to be analyzed, the shape, the size and the effective length of the flow path, and the separation medium. It is desired that the above-mentioned electric field is |10| V/cm or more, preferably |50| V/cm or more, in an absolute value, from the viewpoint of stable electrophoresis of the sample, and |100000| V/cm or less, preferably |10000| V/cm or less, from the viewpoints of durability of chips and generation of Joule heat.

The electric field can be generated using, for instance, commonly used power supply and relay system.

The microchip includes, but is not particularly limited to, concretely, for instance, as described in Examples and the like set forth below, a chip comprising an upper plate and a lower plate, wherein:

(A) the lower plate has thereon two orthogonal channels of 1 to 200 μm in width and 0.5 to 100 μm in depth,
(B) the upper plate has four reservoirs of 0.5 to 4 mm in both diameter and depth, and (C) any one of the reservoirs as defined in (B) being arranged at a position corresponding to each end of the channels as defined in (A), and wherein the reservoir is a reservoir to which electric field can be applied.

In the method for analyzing a nucleic acid of the present invention, there can be used, for instance, a microchip comprising a sample-injection member, a channel for sample analysis and a reservoir for an electrode.

The shapes of the sample-injection member of a microchip electrophoresis device include, as shown in FIG. 11, cross, double-cross, T-shape, double T-shape, and direct connection-type to the channel for analysis.

The channel in the above-mentioned (A) is a microchannel used for separation of the nucleic acid. The width of the above-mentioned channel can be appropriately set depending upon the size of the microchip, purposes of use and the like. Concretely, it is desired that the width of the above-mentioned channel is 1 μm or more, preferably 10 μm or more, from the viewpoint of sufficiently obtaining analysis sensitivity of the sample, and that the width is 200 μm or less, preferably 150 μm, from the viewpoint of microfluid dynamics. In addition, the depth of the above-mentioned channel can be appropriately set depending upon the size of the microchip, purposes of use and the like. Concretely, it is desired that the depth is 0.5 μm or more, preferably 5 μm or more, from the viewpoint of analysis sensitivity of the sample, and that the depth is 100 μm or less, preferably 50 μm, from the viewpoint of microfibricating technique. Furthermore, the length of the above-mentioned channel for sample separation can be appropriately set depending upon the size of the microchip, the nucleic acid to be separated and the like, and its desired that the length is longer than the effective length. The effective length is a distance from the crossing portion of the channel to a sample detection point. It is desired that the length is 0.5 mm or more, preferably 1 mm or more, from the viewpoint of stable electrophoresis of the sample, and that the length is 70 mm or less, preferably 35 mm or less, from the viewpoint of superiority to the existing capillary system.

In addition, the size of the reservoir in the above-mentioned (B) can be appropriately set depending upon the applied voltage and the applied time. Concretely, it is desired that the size of the reservoir is 0.5 mm or more, preferably 1 mm or more, from the viewpoint of maintaining buffer capacity, and that the size is 4 mm or less, preferably 3 mm or less, from the viewpoint of high integration of the chip.

The separation medium during the electrophoresis includes methyl cellulose, hydroxypropyl methyl cellulose (HPMC), hydroxyethyl cellulose (HEC), hydroxypropyl cellulose (HPC), polyethylene glycol (PEG), polyethylene oxide (PEO), polyacrylamide (PAA), polyvinyl pyrrolidone (PVP), dextran, agarose and the like. The above-mentioned separation medium can be used alone or in admixture. Methyl cellulose is desirable, from the viewpoint of low overlapping concentration. It is desired that the substance is a solution of polymer not having a cross-linking point, from the viewpoint of repeated use of the microchip.

In general, in order to separate a nucleic acid, for instance, a polymer compound such as DNA, a separation medium such as gel or a polymer is required. There has also been reported separation with a free solution not using a separation medium. In the present invention, the separation may be also carried out with the free solution not using the separation medium.

For instance, when electrophoresis is carried out using the microchip described in Examples and the like set forth below, it is desired that the channel of the microchip holds at least one member selected from the group consisting of methyl cellulose, hydroxypropyl methyl cellulose (HPMC), hydroxyethyl cellulose (HEC), hydroxypropyl cellulose (HPC), polyethylene glycol (PEG), polyethylene oxide (PEO), polyacrylamide (PAA), polyvinyl pyrrolidone (PVP), dextran and agarose.

It is desired that pH of the above-mentioned separation medium is 1 to 12, from the viewpoints of stable maintenance of the nucleic acid and durability of the chip.

Concrete example of the above-mentioned separation medium is a separation medium and the like, of which buffer contains 1% by weight of methyl cellulose, and of which buffer is at least one member selected from the group consisting of Tris-borate buffer (pH 8.2), Tris-acetate buffer, TAE (Tris-acetate, EDTA) buffer, TBE (Tris-borate, EDTA) buffer, Tris-hydrochloric acid buffer and phosphate buffer.

The method for analyzing a nucleic acid of the present invention can be also applied to a microchip electrophoresis device made of silica glass, Pyrex glass, a resin such as PMMA, silicon, or any other material, and can be also applied to all the methods for carrying out electrophoresis using a flow path of a microscale or nanoscale.

In the above-mentioned step (a), it is desired that all the procedures are performed at 0° to 80° C., preferably 10° to 35° C., and more preferably 15° to 35° C., from the viewpoints of prevention of dew condensation on the chip surface, suppression of evaporation of the solution from the reservoirs, and influence on the resolution.

More concretely, the procedures for step (a) in the method for analyzing a nucleic acid of the present invention are roughly divided into three steps: a) a sample-loading, b) a sample-injection, and c) a sample-separation. Each step will be explained hereinbelow with reference to the system shown in FIG. 1 as an example.

a) Sample-Loading Step:

Each channel is filled with a 50 mM Tris-borate buffer (pH 8.2) containing 1% by weight methyl cellulose. A 0.8 μl DNA sample solution is introduced into the reservoir R1, and the reservoirs R2, R3 and R4 are filled with 1 μl of Tris-borate buffer (pH 8.2). The DNA sample is applied to the channel crossing portion, with keeping the following potentials for 20 seconds at each of the reservoirs: R1: −0.40 kV, R2: GND, R3: −0.55 kV, and R4: −0.95 kV.

b) Sample-Injection Step:

The potentials are changed for 1 second to R1: −0.40 kV, R2: −0.4 kV, R3: −0.66 kV, and R4: GND, thereby injecting a sample plug to a separation channel.

c) Sample-Separation Step:

Pulse electric field having a pulse coefficient of 2 (forward time: backward time=2:1) is applied between electrodes R3 (forward: −0.66 kV, backward: 0.66 kV) and R4 (GND). R1 and R2 are opened to the GND potential. At this time, for instance, when a pulse at a frequency of 10 Hz is applied, the DNA band migrates linearly at a speed of about one-third that in steady electric field (−0.66 kV) in the injection step.

In the above-mentioned step (b), the means for detecting a nucleic acid include laser-excited fluorescence detectors, ultraviolet/visible light absorption detection, fluorescence detection, differential refractive index detection, thermo-optical detection, circular dichroism detection, electrochemical detection, electroconductivity detection and the like.

According to the method for analyzing a nucleic acid of the present invention, since the effective length in electrophoresis can be shortened, the electrophoresis time can be shortened, so that the method is suitable for high-speed analysis of a nucleic acid having physicochemical properties such as molecular weight, nucleic acid conformation polymorphism (especially single-stranded nucleic acid conformation polymorphism), and higher-order structure. Also, even when the higher-order structure of DNA is changed due to modification of a base or the like, the method for analyzing a nucleic acid of the present invention can be applied to the detection of the modified bases.

The present invention is hereinafter described in more detail by means of, but is by no means limited to, the following examples.

EXAMPLE 1

Three kinds of FITC (fluorescein isothiocyanate)-labeled synthetic single-stranded DNA fragments [PAGE (polyacrylamide gel electrophoresis)-purified grade] having the following sequences:
5'-gttggctctgactgtaccac-3' (SEQ ID NO: 1),
5'-gttggctctgactgtaccaccatccactacaactacatgt-3' (SEQ ID NO: 2), and
5'-gttggctctgactgtaccaccatccac-
tacaactacatgtgtaacagttcctgcatgggc-3' (SEQ ID NO: 3), which are parts of the sequence of exon 7 of p53 tumor suppressor gene, were purchased from KURABO INDUSTRIES LTD. These DNA fragments were dissolved in TB buffer [50 mM Tris-borate (pH 8.2)]. The DNA-containing solution obtained was stored at 4° C. until use. A 1% by weight methyl cellulose [4000 cP, 2% by weight solution, manufactured by Sigma Ltd.] was used as a separation medium.

A schematic view of the microcapillary electrophoresis (μ-CE) system is shown in FIG. 1. As the microchip, a microchip manufactured by Shimadzu Corporation was used. The above-mentioned microchip was composed of two plates, in which the lower plate has two orthogonal microchannels (width 50 μm, depth 20 μm), and the upper plate has four wells (diameter and depth 1 mm) as reservoirs (R1 to R4). The above-mentioned channels were filled with a TB buffer containing 1% by weight methyl cellulose. The channel lengths from each of the reservoirs R1, R2, R3, and R4 to the crossing portion of the channel were 7 mm, 7 mm, 7 mm and 32.5 mm, respectively. A platinum (Pt) wire was inserted into each reservoir. The potentials between the reservoirs were controlled by Labview (manufactured by National Instrument) using power supplies (HV1–5) and the relay system. Pulse electric field was generated by controlling the potential at R3 with respect to R4 (GND) using a high-voltage power supply (HV4) and the function generator (FG).

An arbitrary point in the separation flow path from the crossing portion of the flow path to R4 is referred to as a measurement point, and a distance from the crossing portion to a measuring point is referred to as an effective length. The measurement point is irradiated with an argon-ion laser through a long focal lens of 40-fold magnification, and fluorescence of the FITC-stained sample passing this point is detected by PMT through a dichroic mirror. The PMT signal is inputted to the analyzing device to obtain an electrophoretogram.

Prior to these procedures, in order to obtain potential relationship between the reservoirs according to the conditions of the size and the shape of the flow path, and the separation medium, the illumination/signal detection portion of the above-mentioned device was modified to illuminate the flow path with a mercury lamp to a lens of 4-fold magnification, and images of the sample injected from the crossing portion to the channel for separation were taken by an SIT camera. See, for instance, [Ueda, M. et al., *Bioimages* 1999, 7(4), 157–161; Ueda, M. et al., *Electrophoresis* 2000, 21, 176–180].

EXAMPLE 2

Investigation of Conditions for Electric Field Inversion Type Macrochip Electrophoresis (μ-CE)

1) Procedures

The procedures for sample analysis according to electric field inversion type microchip electrophoresis (μ-CE) are roughly divided into three steps: a) sample-loading, b) sample-injection, and c) sample-separation. In order to obtain appropriate relationships in the potentials between the reservoirs in each of these steps and an appropriate frequency region in the electric field inversion process, a sample migrating in the flow path was directly observed, and motion picture analysis was carried out. On the bases of these data, it was confirmed that an appropriate pherogram was obtained in the frequency region determined by the motion picture analysis using the device having the construction shown in FIG. 1. Under these conditions, separation experiments of the samples were carried out, and it was found that excellent separation was achieved by electric field inversion. All the experiments in μ-CE described below were carried out at 25° C.

Figure 2:
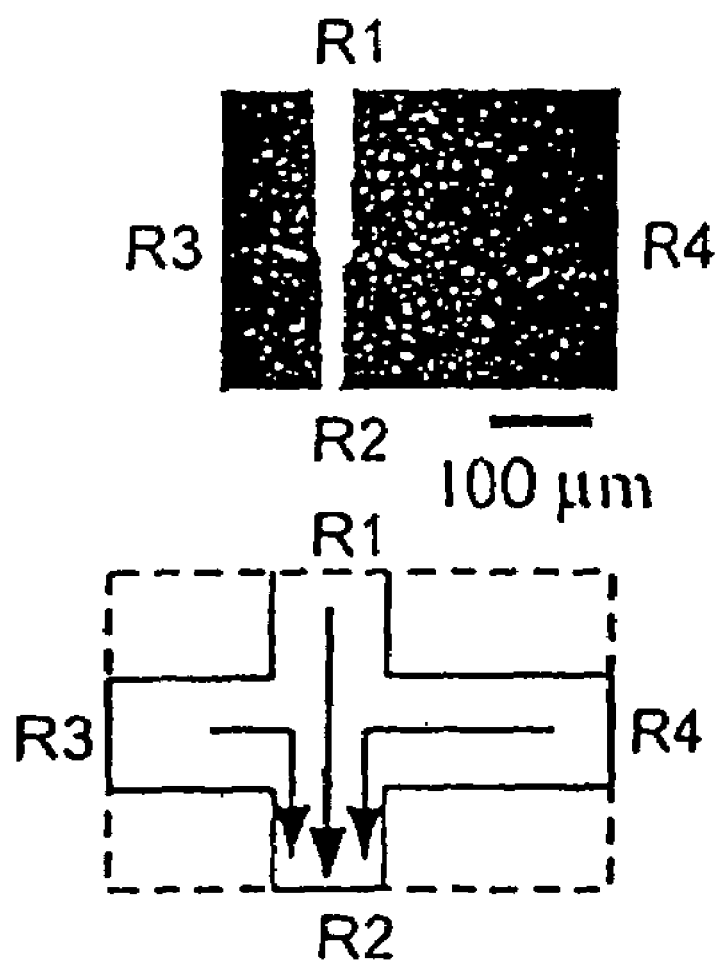
FIG. 2 is a schematic view showing the migration of a DNA sample during the sample-loading step of electric field inversion type microchip electrophoresis. The potentials at each of the reservoirs are: R1: −0.40 kV, R2: GND, R3: −0.55 kV, and R4: −0.95 kV.
Figure 3:
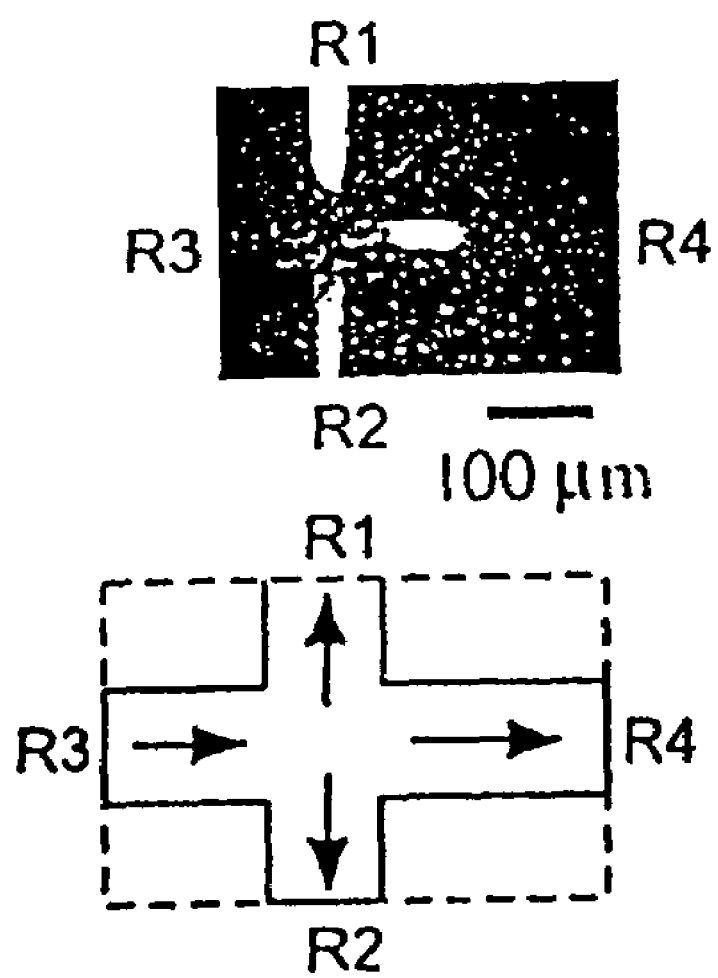
FIG. 3 is a schematic view showing the migration of a DNA sample during the sample-injection step of electric field inversion type microchip electrophoresis. The potentials at each of the reservoirs are: R1: −0.40 kV, R2: −0.4 kV, R3: −0.66 kV, and R4: GND.
Figure 4:
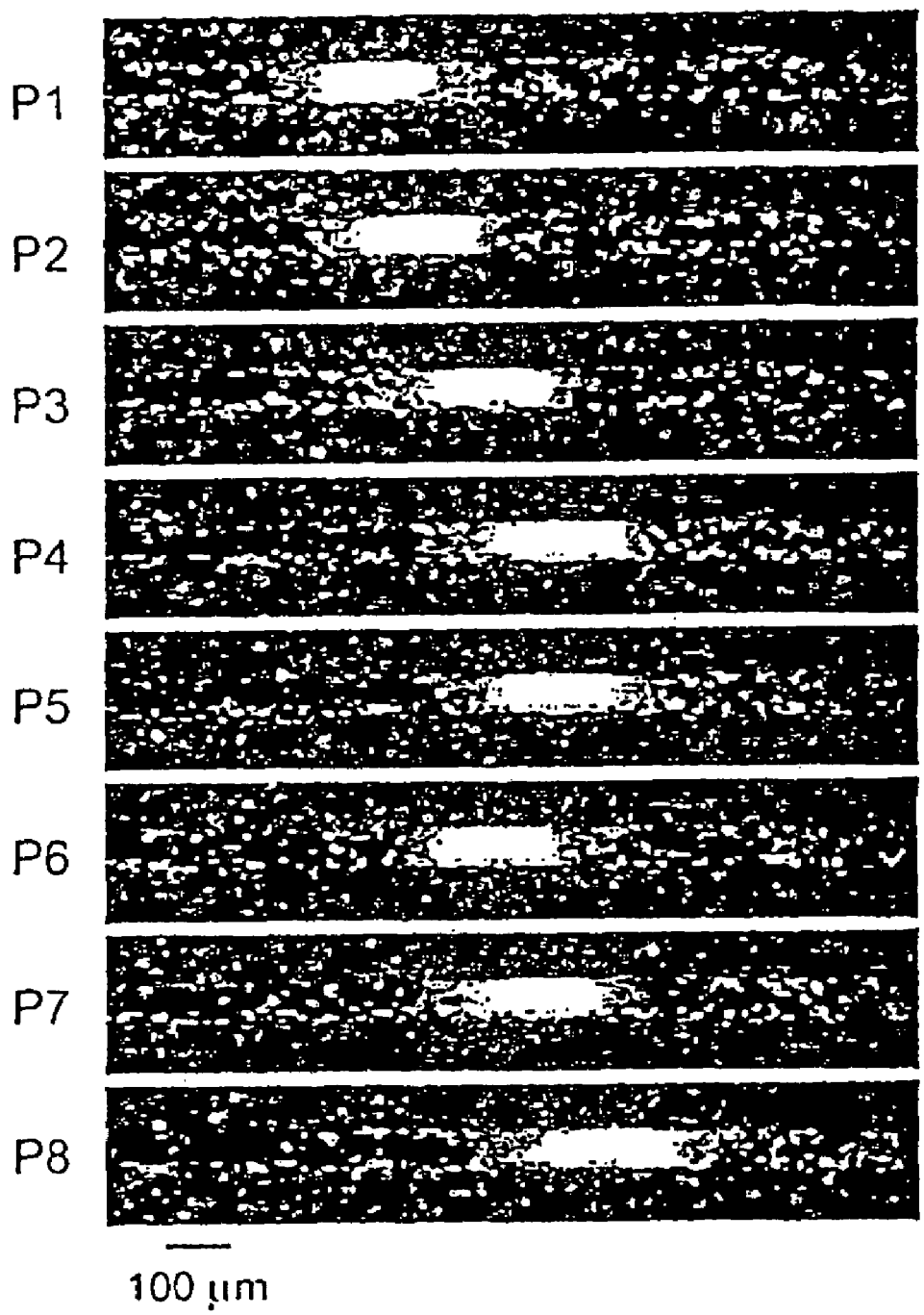
FIG. 4 is a schematic view showing the migration of a DNA sample during the sample-separation step of electric field inversion type microchip electrophoresis. Pulse electric field (pulse coefficient of 2; 1 Hz) is applied between R3 (±0.66 kV) and R4 (GND). R1 and R2 are opened to GND. Each of the images obtained at an interval of 0.2 seconds is shown in P1 to P8.
Figure 5:
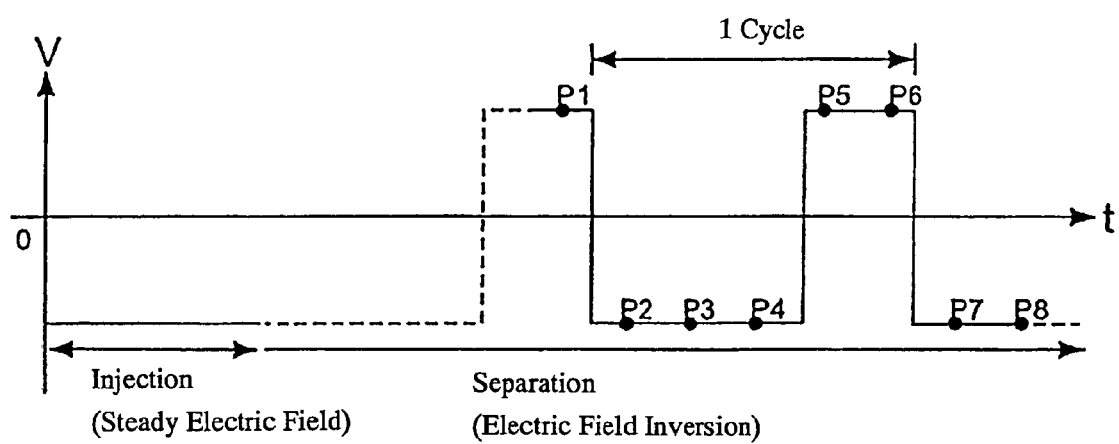
FIG. 5 is a schematic view showing the potentials at R3 during the sample-injection step (steady electric field) and the sample-separation step (electric field inversion). In the figure, P1 to P8 correspond to those in FIG. 4.
Figure 6:
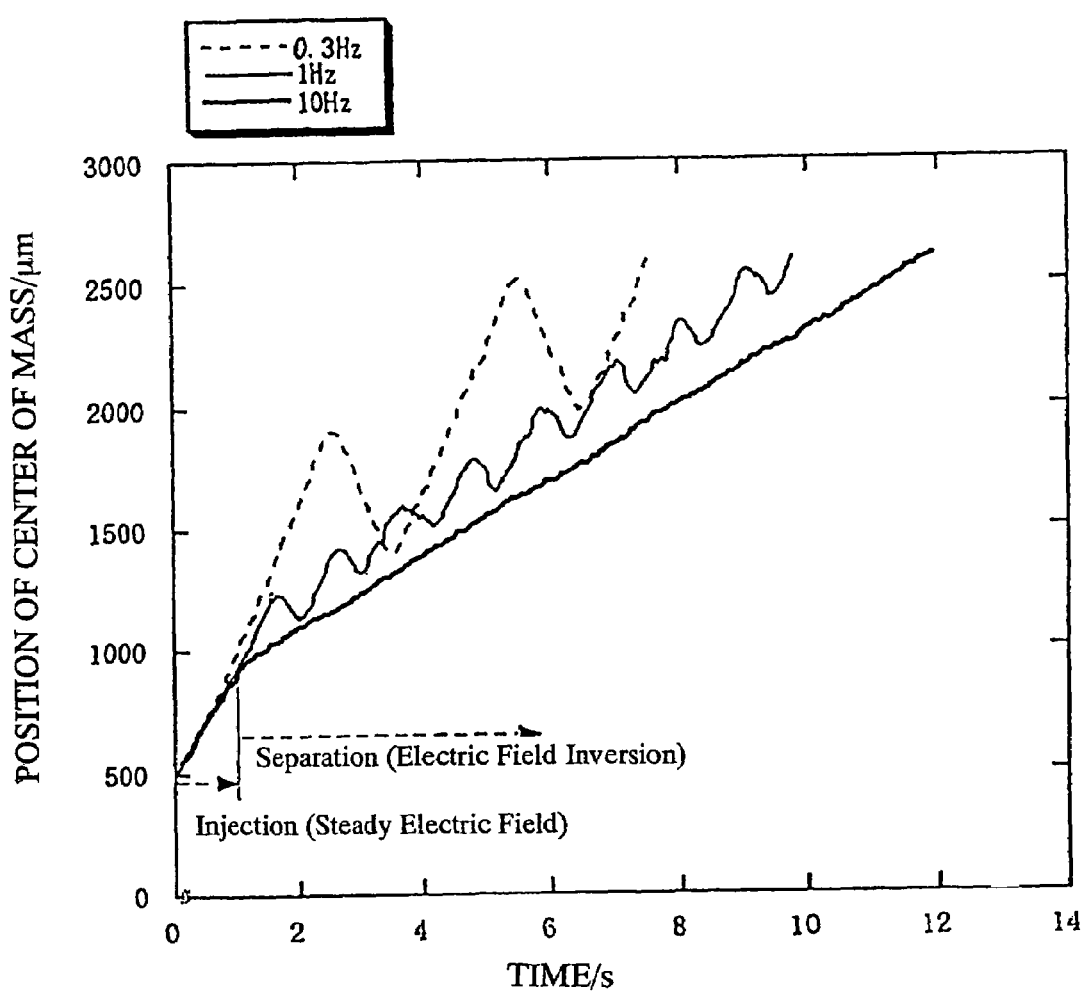
FIG. 6 is a diagram showing the time evolution of a sample plug after the injection step in steady electric field for 1 second. The dotted line, thin solid line and bold solid line represent the time evolution of the sample plug in pulse electric fields at 0.3 Hz, 1 Hz and 10 Hz, respectively.

2) Investigation of Electric Field Conditions by Direct Observation Method a) Sample-Loading:

A 0.8 μl DNA sample solution was applied to the reservoir R1, and the reservoirs R2, R3 and R4 were filled with 1 μl of TB buffer. The DNA sample was loaded to the crossing portion of the flow path by maintaining the following potentials at each of the reservoirs for 20 seconds: R1: −0.4 kV, R2: GND, R3: −0.55 kV, and R4: −0.95 kV. FIG. 2 shows a sample-loading step imaged by the SIT camera, and the directions of migration of negatively charged ions in the flow path are indicated by arrows. It can be seen from FIG. 2 that there are relationships in the potentials such that the sample concentration occurs in the crossing portion, and that the sample outflow into R3 and R4 does not occur.

b) Sample-Injection:

In order to inject a sample plug in the channel for separation, the potentials at each of the reservoirs were switched to and kept for 1 second at the following potentials: R1: −0.40 kV, R2: −0.4 kV, R3: −0.66 kV, and R4: GND. FIG. 3 schematically shows a fluorescence image of the sample-injection process and the movement of negatively charged ions. It can be seen from FIG. 3 that the sample plug is injected into the channel for separation in this electric field, and the sample inflow from R1 and R2 does not occur.

c) Sample-Separation (Non-Steady Electric Field Process):

The potentials at R1 and R2 were opened to R4 (GND). A rectangular wave electric field (forward: −0.66 kV, backward: 0.66 kV) having a pulse coefficient of 2 (time weight: forward/backward=2/1) was supplied between R3 and R4 (GND). Under these conditions, the frequency of the electric field was changed within the range from 0.1 Hz to 50 Hz, and the migration behavior of the sample plug was determined by image analysis. FIG. 4 shows a fluorescent image of sample DNA (20-mer) migrating in the electric field inversion process (pulse coefficient: 2, frequency: 1 Hz). P1 to P8 in FIG. 4 correspond to P1 to P8 in the schematic view of inverted electric field shown in FIG. 5. FIG. 6 shows the time evolution of the position of the center of mass of the sample plug thus obtained at 0.3 Hz, 1 Hz, and 10 Hz. From the results, it can be considered that the backward migration by the electric field inversion is very small at 10 Hz, so that the sample plug as a whole is migrated by steady electric field in about one-third the strength of the steady electric field in the injection process (−0.66 kV).

3) Investigation of Frequency of Inverted Electric Field by Pherogram

The frequency of the electric field investigated in the above-mentioned 2) was investigated by obtaining a pherogram from the device having the construction shown in FIG. 1.

Electric field inversion type microchip electrophoresis was carried out at frequency conditions of 0.3 Hz, 1 Hz and 10 Hz, according to the above-mentioned 2) using the above-mentioned 20-mer ssDNA. The results are shown in the panels a), b) and c) of FIG. 7, respectively.

Figure 7:
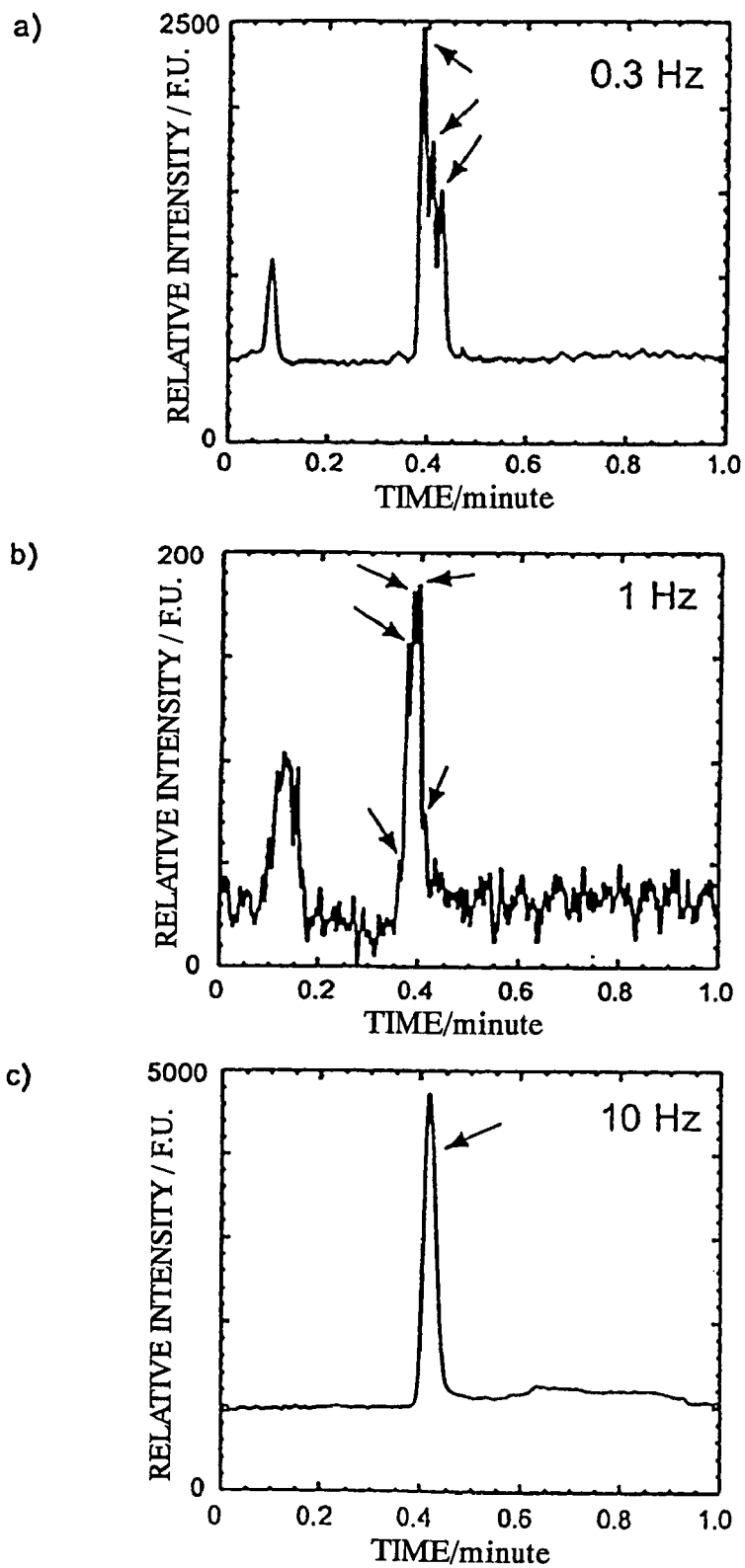
FIG. 7 shows electrophoretograms of a DNA fragment (20-mer) at each of the frequencies. Panel a) shows the results for 0.3 Hz, Panel b) shows the results for 1 Hz, and Panel c) shows the results for 10 Hz.

As shown in the panel a) of FIG. 7, it can be seen that the three peaks indicated by arrows appear at a frequency of 0.3 Hz. In the μ-CE system used in this Example, the size of the laser spot is about 10 μm. On the other hand, as shown in FIG. 6, the backward electrophoresis distance is about 500 μm. Therefore, it can be considered that the DNA band crosses over the laser spot a number of times to generate dummy peaks.

In the case of 1 Hz, peak occurrence becomes further complicated, as shown in the panel b) of FIG. 7.

At 10 Hz, however, the backward electrophoresis distance is made shorter, and the DNA band steadily migrated as shown in FIG. 6. It can be seen from the monotony migration pattern that the single peak shown in the panel c) of FIG. 7 is obtained.

Next, with regard to the case of the 20-mer ssDNA, peak width at the external frequencies of 0.1 Hz or more was examined in order to optimize external frequency. A band width Δ and a height h of the relative intensity peak ascribed to the same DNA fragment at a migration time t were obtained, a relative band width $\Gamma=\Delta/ht$ was calculated, and a half value of width Δ was normalized with the peak height h and the migration time t. The results are shown in the form of a graph of the relationship between the relative band width $\Gamma$ and the external frequency in FIG. 8. The dotted line in FIG. 8 represents a relative band width in a steady electric field.

Figure 8:
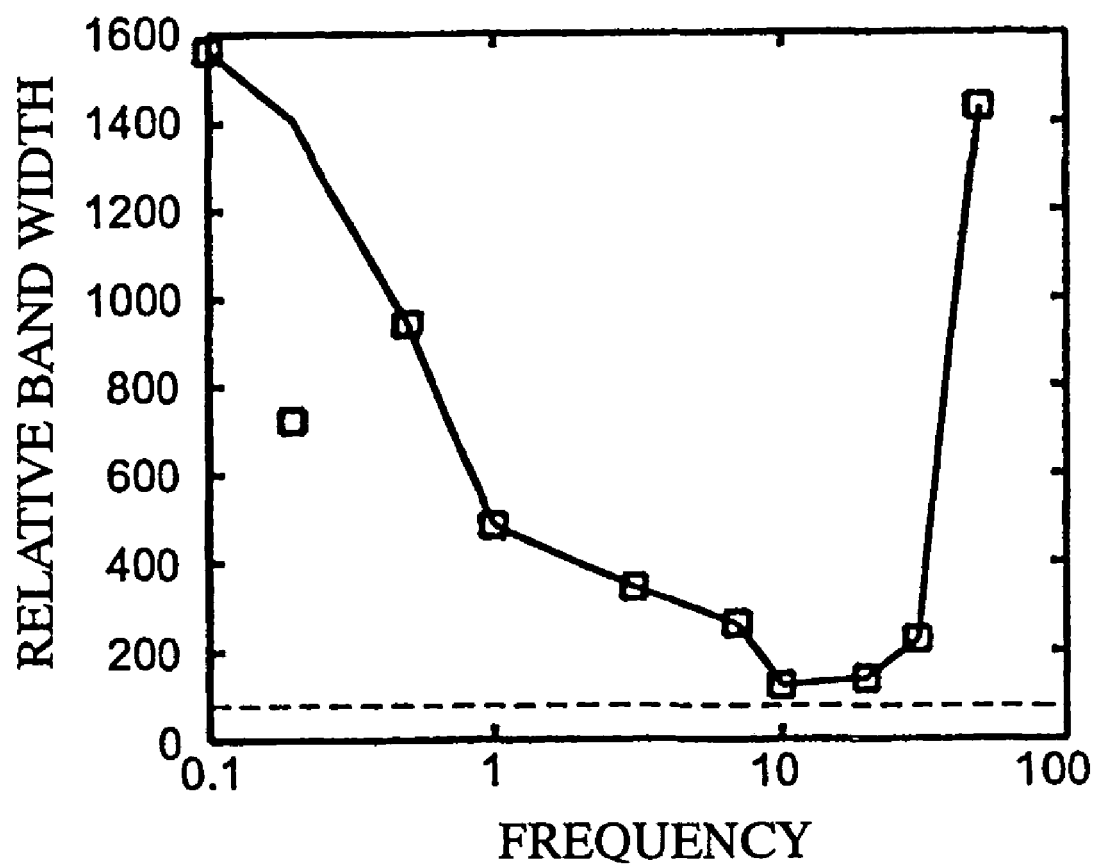
FIG. 8 is a schematic view of relative band width with respect to frequency. The dotted line is a value in steady electric field. The solid line shows a 20% smooth line.

As shown in FIG. 8, dummy peaks cause apparent band broadening in the region of less than 10 Hz.

Additionally, in the case of ssDNA of about 20-mer length as in the present experiment, it is shown that the relative band width has a minimum in the range from 10 Hz to 20 Hz, and the band width at the minimum is 1.4 times greater than that obtained in the steady electric field. The band narrowing induced by electric field inversion on long-chain DNA having a size of about 40 kbp was not observed under the present experimental conditions. These tendencies are considered to depend on the length of the DNA to be analyzed, and the like.

As described above, it is suggested that electric field inversion is effective for the separation of the DNA fragments at frequencies of 10 Hz or more.

Figure 9:
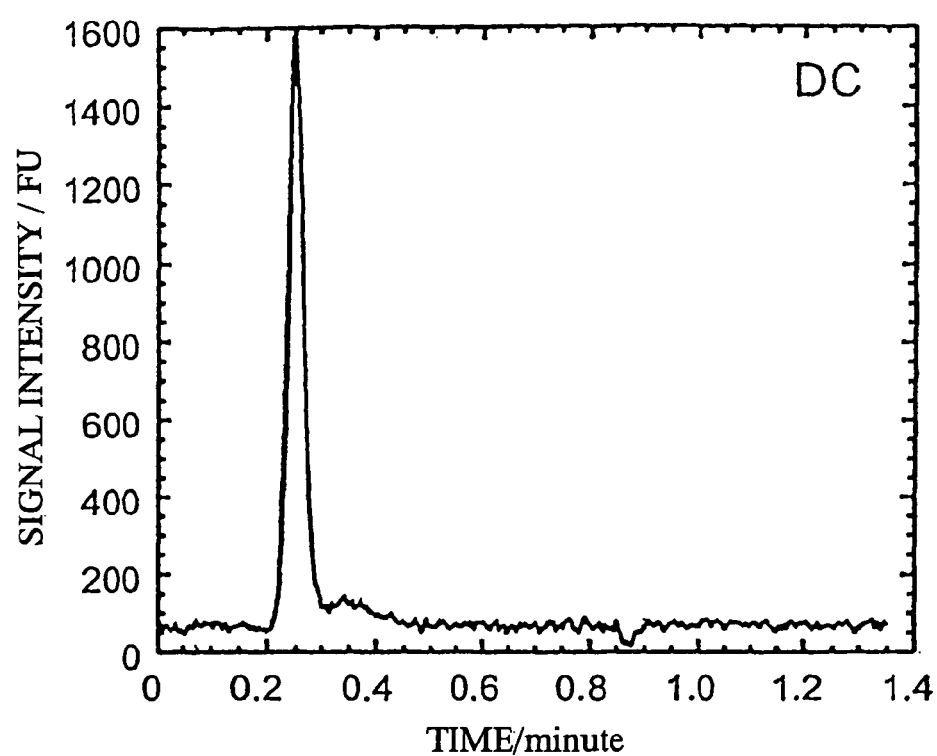
FIG. 9 shows electrophoretograms in steady electric field and pulse electric field. The samples are each of 20-mer, 40-mer, and 60-mer ssDNA. The effective length is a distance from the crossing portion of the flow path to the sample detection point, and is 6 mm. Panel a) is an electrophoretogram in steady electric field (167 V/cm), and Panel b) is an electrophoretogram in a pulse electric field (10 Hz, pulse coefficient of 2, ±167 V/cm).
Figure 9:
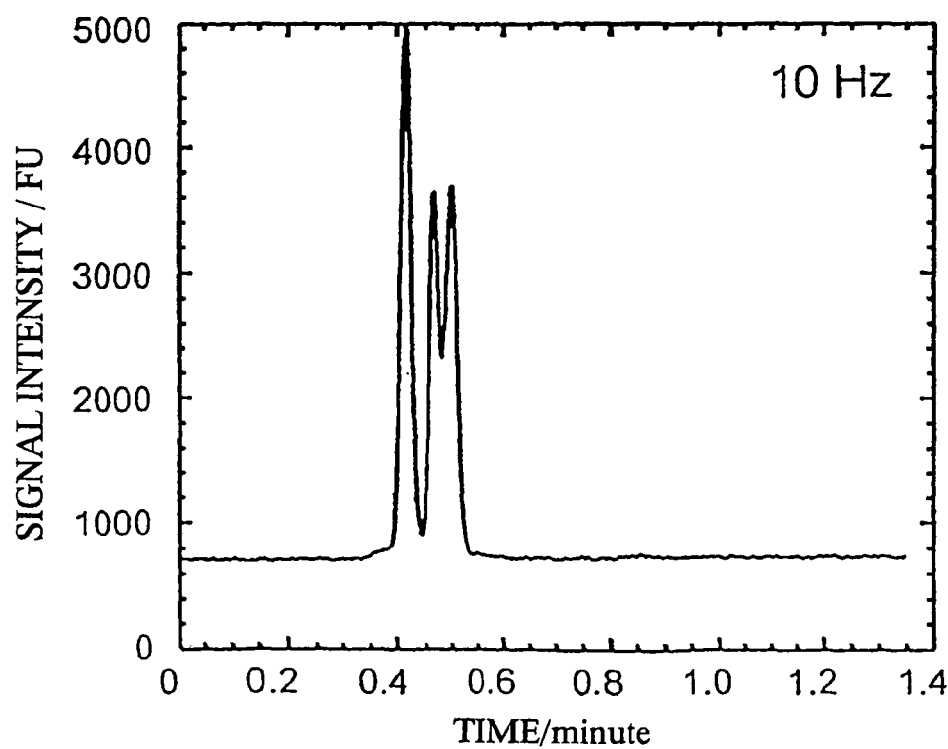

The panels a and b of FIG. 9 show electrophoregrams of ssDNA fragments (20-mer, 40-mer and 60-mer) in each of steady electric field (167 V/cm) and a 10 Hz pulse electric field (±167 V/cm, pulse coefficient of 2). The effective length is 6 mm for both cases. Although a longer separation time was required in electric field inversion type microchip electrophoresis as compared to the migration in the steady electric field, the separation was achieved with an effective length of 6 mm. Usually, the mechanism for the separation of long-chain DNA in electric field inversion type electrophoresis is discussed using a reptation model [Kim, Y. et al., *Electrophoresis* 1996, 17, 152–160; Heller, C. et al., *Electrophoresis* 1995, 16, 1423–1428; Viovy, J. L., *Phys. Rev. Lett.*, 1988, 60, 855–858]. However, in the present Example, the experiments were carried out in the Ogston region [Rodbard, D. et al., *Proc. Natl. Acad. Sci. USA*, 1970, 65, 970–977]. Although inverted electric fields in the Ogston region have no useful effect in commonly used capillary electrophoresis [Kim, Y. et al., *Electrophoresis* 1997, 18, 2901–2908], the electric field inversion type microchip electrophoresis of the present invention is effective in reducing the effective length for the separation even in the Ogston region.

It is suggested that the electric field inversion type microchip electrophoresis in the Ogston region as described herein has a great possibility for application on the detection of SSCP (single-strand conformation polymorphism), from the viewpoint that the electrophoresis is effective for separating a single-stranded DNA having a relatively short chain length of about 100 nucleotides with a shorter effective length.

SEQUENCE FREE TEXT

SEQ ID NO: 1 shows a nucleotide sequence for a synthesized oligonucleotide (20-mer), which is a part of the sequence of exon 7 of p53 tumor suppressor gene.

SEQ ID NO: 2 shows a nucleotide sequence for a synthesized oligonucleotide (40-mer), which is a part of the sequence of exon 7 of p53 tumor suppressor gene.

SEQ ID NO: 3 shows a nucleotide sequence for a synthesized oligonucleotide (60-mer), which is a part of the sequence of exon 7 of p53 tumor suppressor gene.

INDUSTRIAL APPLICABILITY

According to the method for analyzing a nucleic acid of the present invention, a nucleic acid, especially a single-strand conformation polymorphism, can be analyzed more conveniently in a short time period. Therefore, the method for analyzing a nucleic acid of the present invention is useful for the diagnosis and treatment of diseases such as detection of gene diseases and application to Taylor-made therapy.

The invention claimed is:

1. A method for analyzing a nucleic acid in a microcapillary electrophoresis comprising the steps of:
   (a) carrying out electric field inversion during electrophoresis on a microchip, thereby separating each of the nucleic acids having different physicochemical properties, and
   (b) detecting the nucleic acid separated by the above step (a), wherein an effective length in electrophoresis is 0.5 to 70 mm.

2. The method for analyzing a nucleic acid according to claim 1, wherein a forward/backward time weight in the electric field inversion is 1/1 to 10/1.

3. The method for analyzing a nucleic acid according to claim 1, wherein the electric field inversion is carried out by applying an electric field at a frequency of at least 10 Hz.

4. The method for analyzing a nucleic acid according to claim 1, wherein the electric field has the strength of |10| to |100000| (absolute value) V/cm.

5. The method for analyzing a nucleic acid according to claim 1, wherein the microchip is a microchip comprising a sample-injection member, a channel for sample analysis and a reservoir for an electrode.

6. The method for analyzing a nucleic acid according to claim 5, wherein the microchip is a chip comprising an upper plate and a lower plate, wherein:
   (A) the lower plate has thereon two orthogonal channels of 1 to 200 μm in width and 0.5 to 100 μn in depth,
   (B) the upper plate has four reservoirs of 0.5 to 4 mm in both diameter and depth, and
   (C) the reservoirs as defined in (B) are arranged at positions corresponding to each end of the channels as defined in (A), and wherein an electric field can be applied to the reservoir.

7. The method for analyzing a nucleic acid according to claim 6, wherein the channel holds a separation medium containing at least one member selected from the group consisting of methyl cellulose, hydroxypropyl methyl cellulose (HPMC), hydroxyethyl cellulose (HEC), hydroxypropyl cellulose (HPC), polyethylene glycol (PEG), polyethylene oxide (PEO), polyacrylamide (PAA), polyvinyl pyrrolidone (PVP), dextran and agarose.

8. The method for analyzing a nucleic acid according to claim 7, wherein pH of the separation medium is 1 to 12.

9. The method for analyzing a nucleic acid according to claim 7 or 8, wherein the separation medium contains 1% by weight of methyl cellulose, of which buffer is at least one member selected from the group consisting of Tris-borate buffer, Tris-acetate buffer, TAE (Tris-acetate, EDTA) buffer, TBE (Tris-borate, EDTA) buffer, Tris-hydrochloric acid buffer and phosphate buffer.

10. The method for analyzing a nucleic acid according to claim 1, wherein a physicochemical property is at least one member selected from the group consisting of nucleic acid conformation polymorphism, molecular weight and higher-order structure.

11. The method for analyzing a nucleic acid according to claim 1, wherein the nucleic acid in the step (b) is detected by at least one member selected from the group consisting of ultraviolet/visible light absorption detection, fluorescence detection, differential refractive index detection, thermo-optical detection, circular dichroism detection, electrochemical detection and electroconductivity detection.

12. The method for analyzing a nucleic acid according to claim 1, wherein the effective length in electrophoresis is 0.5 to 35mm.

13. The method for analyzing a nucleic acid according to claim 1, wherein the nucleic acids having different physicochemical properties are from 20 nucleotides to about 100 nucleotides in length.

* * * * *